United States Patent [19]

Schultz

[11] Patent Number: 5,171,886

[45] Date of Patent: Dec. 15, 1992

[54] PREPARATION OF 2,2'-OXYDISUCCINATE

[75] Inventor: Robert G. Schultz, St. Louis, Mo.

[73] Assignee: Monsanto Company, St. Louis, Mo.

[21] Appl. No.: 613,439

[22] Filed: Nov. 15, 1990

[51] Int. Cl.$^5$ ............................................ C07C 59/305
[52] U.S. Cl. .................................................... 562/583
[58] Field of Search ......................................... 562/583

[56] References Cited

U.S. PATENT DOCUMENTS

| | | | |
|---|---|---|---|
| 3,635,583 | 1/1972 | Lamberti et al. | 252/152 |
| 3,692,685 | 9/1972 | Lamberti et al. | 252/89 |
| 3,914,297 | 10/1975 | Lamberti et al. | 260/535 |
| 4,798,907 | 1/1989 | Macbrair, Jr. et al. | 562/583 |
| 4,959,496 | 9/1990 | Crutchfeld et al. | 562/583 |

OTHER PUBLICATIONS

Hydroxy Dicarboxylic Acids, J. H. Van Ness, vol. 13, pp. 103–120, 1965.
Kinetics of the Acid Catalysis of the Hydration of Fumaric Acid to Malic Acid, Lee T. Rozelle & Robert A. Alberty, Dec. 1957, pp. 1637–1640.

Primary Examiner—Jose G. Dees
Assistant Examiner—B. Frazier
Attorney, Agent, or Firm—Richard H. Shear; James C. Bolding; Raymond C. Loyer

[57] ABSTRACT

There is disclosed herein an improved processes for the preparation of oxydisuccinate by reacting in an alkaline reaction medium the salts of maleic acid and malic acid in the presence of a calcium ion catalyst wherein unreacted maleic acid salts are recovered from the reaction medium as sodium hydrogen maleate by lowering the pH of the reaction product to a range of from about 4 to 6. The precipitated sodium hydrogen maleate salts are recycled to the synthesis reaction as salts of malic acid by hydration in the presence of a hydration catalyst to prepare additional amounts of product.

14 Claims, No Drawings

PREPARATION OF 2,2'-OXYDISUCCINATE

This invention relates to a process for making ether carboxylic acids and more particularly to processes for making ether carboxylates prepared by a calcium ion catalyzed reaction in alkaline medium of maleic and malic acid salts. Such reactions are of the type typically referred to as Michael condensation reactions.

Polycarboxylic acids have long been known to be useful, usually in the salt form, as detergent builders or sequestrants. Also, ether carboxylates useful as metal sequestering and detergent builders have been known and are most desirable for their beneficial effects in laundering applications.

Because ether carboxylates have such effective sequestering ability they have become attractive in recent times for the replacement of sodium tripolyphosphate which has long been the leading detergent builder or sequesterant. Examples of prior art efforts to provide ether carboxylate detergent builders or sequesterants are found in U.S. Pat. Nos. 3,635,830; 3,692,685 which relate to the use of oxydisuccinic acid salts particularly 2,2'-oxydisuccinate salts (ODS) as detergent builders. Another example of an ether polycarboxylate detergent builder or sequesterant is found in U.S. Pat. No. 3,914,927 which relates to carboxymethyl oxysuccinates.

While many carboxylate compounds in the prior art have utility as a builder or sequesterant in laundry detergent formulations, it has been found that certain ether carboxylates are more attractive and cost effective for such utility. In the field of detergent builders and sequesterants for laundry detergent formulations low cost of the components is extremely important because it is in a very competitive market. While many ether carboxylate compounds have been found to be useful there is needed more economical manufacturing processes whereby such compounds can be economically produced in large volume.

The synthesis of many ether carboxylates, including the oxydisuccinates, is achieved in an equilibrium reaction wherein starting materials, tartrate or malate and maleate salts, remain in solution at the end of the reaction. In many cases these starting materials are removed only by solvent extraction which is expensive and not ecologically attractive. Large scale production of such ether carboxylates incur large costs for recovery of reactants and an ecologically and environmentally acceptable means for recovering unreacted starting material is practically a requirement for industrial production of commercial quantities of these ether carboxylates.

There has previously been discovered a process for preparing ether carboxylates by the reaction of the salts of malic acid and maleic acid, said reaction catalyzed by calcium ions and conducted under alkaline conditions wherein unreacted salts are conveniently recovered in such manner that they may be recycled to the synthesis reaction to produce additional ether carboxylate. It was discovered that at a limited range of acidity certain unreacted salts are conveniently recovered from the reaction mixture at the conclusion of the reaction. By reducing the pH of the reaction mixture to a range within about 4 to about 6 by combining a suitable acid with the reaction mixture, the insoluble salts of starting acids precipitate while the desired ether carboxylate product remains in solution. The precipitate is removed by known means such as filtration thereby allowing further processing of the ether carboxylate solution. Such further processing will depend, of course, upon the particular ether carboxylate produced.

To conduct the above mentioned process for preparing ODS in an efficient manner the insoluble salts of maleic and malic acids are recycled to provide further ODS product. When the acidification of the reaction mixture to a pH in the range of from about 4 to about 6 is performed with maleic acid one of the insoluble precipitates formed is sodium hydrogen maleate derived from the unreacted salt of maleic acid. While such salt may be recycled directly or indirectly as the calcium salt to the reactor as described in U.S. Pat. No. 4,959,496 to Crutchfield et al., a more efficient recycle route of the sodium hydrogen maleate has been discovered.

SUMMARY OF THE INVENTION

It has now been discovered that sodium hydrogen maleate recovered from the reaction product in the production of ODS by precipitation with maleic acid can be employed to efficiently provide malic acid salt by hydration either alone or together with maleic anhydride. The malic acid salt is then introduced into the reactor together with maleic acid salt to provide additional amounts of ODS.

Catalysts are optionally employed to increase the rate of conversion to malic acid salt. Such catalyst is usually a mineral acid such as sulfuric or hydrochloric acid or an acid salt such as calcium nitrate.

The hydration reaction takes place at elevated temperatures in the range of from about 100° C. to about 175° C. and usually about 150° C. With sufficient catalyst present the hydrolysis reaction takes place at about the same rate as when only the maleic anhydride is present. The reaction rate for the hydration of maleate to malate is favored or increased by employing elevated temperatures. Thus, the hydration reaction rate is somewhat higher at temperatures in the range of from about 150° C. to about 160° C.

DETAILED DESCRIPTION OF THE INVENTION

Calcium catalyzed reactions for the production of ether carboxylates are known. A typical prior art example of such a process is disclosed in U.S. Pat. No. 4,798,907 MacBriar et al and such patent is hereby incorporated by reference.

ETHER CARBOXYLATE SYNTHESIS

It is typical of the Michael condensation reactions to provide the most effective equilibrium state for the production of the desired compound or mixture by control of the reactant ratio. For example, high ratios of maleic acid salts to malate acid salt in the range of 2 to 1 or greater respectively provide the more optimum production of ODS in the calcium ion catalyzed reaction disclosed in the European publication referred to above. However, a significant amount of unreacted maleate salt remains in solution at the end of the reaction together with the desired ODS.

The recovery of unreacted maleate salts from calcium catalyzed reactions of maleic acid salts with salt of malic acid in alkaline medium is conveniently achieved by acidifying the reaction product so as to reduce the pH to within the range of about 4 to about 6. However it has been found that the salts of malic acid in the reaction mixture are least soluble at a pH in the range of from about 7 to about 8.5 and such salts become increasingly soluble as the pH is reduced further to the above mentioned range of from about 4 to about 6. Preferably, the acid addition to the reaction mixture is interrupted when the pH of the reaction mixture reaches slightly below 8. The precipitated salts are then removed before reducing the pH to the desired lower level of from about 4 to about 6. The lower range is optimum for precipitation and removal of the maleic acid salts in the form of sodium hydrogen maleate. The lower pH range also provides removal of a majority of the malic acid salts but it has now been discovered that the malic acid salts which have precipitated during acid addition for the purpose of lowering the pH to a range between about 4 and about 6 begin to redissolve into the reaction mixture before completion of the process of acid addition and removal of the precipitate. To remove the maximum amount of malic acid salts it is necessary to interrupt acid addition at the higher pH range and remove precipitated acid salts. Even though malic salts are removed at the higher pH range, it has been found that the precipitation and removal of further amounts of malic acid salts still occurs together with the precipitation of the sodium hydrogen maleate salt at the lower pH range of from about 4 to about 6.

A particular advantage of the process of this invention, whereby unreacted maleate salt is recovered, is the ability to regulate the reactant ratios more freely since convenient recovery and recycle is possible. Loss of unreacted maleate salt is insignificant and its recovery economical, particularly when maleic acid is employed to reduce the pH of the reaction product of the condensation reaction. High maleate to malate ratios such as in excess of 1 to 1 respectively have been found to result in the reduction or even elimination of the maturation step usually required in the production of ODS. Therefore, a preferred embodiment of this invention is the calcium catalyzed reaction of maleate and malate salts in alkaline medium wherein the ratio of maleate to malate salt is in excess of 1.

Small amounts of by-products such as fumarate and residual amounts of ODS trapped in the precipitate are not deleterious to the use of this recycled precipitate in subsequent condensation synthesis reaction.

Sodium hydrogen maleate may be recycled to the hydration reactor alone or in admixture with additional maleic acid (or anhydride $+H_2O$) to provide the amount of substrate required to produce the needed amount of malic acid. If the amount of sodium hydrogen maleate is greater than that needed for hydration to malic acid, the excess sodium hydrogen maleate may be recycled to the ODS synthesis reaction, preferably in accordance with the procedure described in U.S. Pat. No. 4,959,496 referred to above and hereby incorporated by reference.

Hydration of maleic acid to form fumaric and malic acid is well known, Kirk Othmer Encyclopedia of Chemical Technology, 3rd Ed., Vol. 13, p. 103–120. However, the recycle of sodium hydrogen maleate in the manufacture of ODS has heretofore been known only for its use as a maleic acid salt.

It has been found that the use of catalyst in the hydration reaction is advantageous because it results in higher conversion of maleate to malic acid. Inorganic, mineral acids and salts are the usual catalysts, for example, sulfuric acid, hydrochloric acid, nitric acid, and preferably calcium nitrate. As will be shown by the following examples, the amount of sulfuric acid required to provide desirable conversion rates is higher in the process of this invention than would be expected from prior experience with maleic anhydride alone.

FORMATION OF ODS

As noted above there has been previously disclosed an ether-bond forming reaction using the combination of sodium and calcium salts in aqueous alkaline ether-bond forming reactions to provide in high yield ether carboxylates. One such disclosure is EPO 0 236 007. The ether carboxylate is formed in a reaction mixture containing sodium and calcium salts of maleic acid and malic acid which react to form the sodium and calcium salts of ODS. The reaction takes place at temperatures below about 120° C. in aqueous medium wherein one component is the maleate salt and the other is the malate salt. The reaction mixture also contains an inorganic reactant component consisting essentially of at least one inorganic base or mixture thereof. The reaction mixture is held at a temperature of at least about 60° C. for a period sufficient to permit a major portion of the ether-bond formation between the maleate and malate present in the reaction mixture. According to previously known reactions the malate to maleate molar ratios range from about 1:0.7 to about 1:2, more preferably from about 1:1.05 to about 1:1.4 at the initial time of combination.

The molar ratio of calcium to maleate plus malate is disclosed in the prior art to be in the range of from about 0.1:1 to about 0.75:1, more preferably from about 0.31:1 to about 0.57:1. Also present in the reaction mixture is sodium which is present at a molar ratio of sodium to maleate plus malate of from about 0.5:1 to about 2.2:1. Ratios of sodium to malate and maleate are adjusted in the event the acid form of these compounds are employed and no organic salts are used. When the acid form of maleate and malate are employed the sodium to maleate plus malate molar ratio is generally in the range of from about 0.9:1 to about 1.48:1. As noted above, the reaction mixture is alkaline generally by the addition of an inorganic base so as to provide from about 0.01 to about 0.4 moles of free hydroxide per mole of combined maleate and malate. Preferably the free hydroxide is present in the range from about 0.04:1 to about 0.2:1 per mole of combined maleate and malate, preferably from 0.04:1 to 0.1:1 respectively. The reaction is reported to have been performed at a pH in the range of from about 9 to about 13 measured by cooling the reaction mixture sample to 25° C. and diluting to about 5% dissolved solids prior to pH measurement.

In accordance with this invention the malate/maleate ratio is reversed such that it is now convenient and economical to operate the reaction to produce ODS with an excess of maleate in the reaction mixture. In general the malate to maleate molar ratios in accordance with the process of this invention can range from about 1:1.5 to 1:3 respectively or even higher. Of course, the excess maleate does not react but is recovered in accordance with this invention for reuse in a convenient manner as will be more fully described below. Calcium hydroxide level is typically in the range of, on a molar basis of malate to calcium hydroxide, from 1:1 to 1:2. Calcium levels affect the reaction rate but have little effect on the ability to recover unreacted starting material in the form of sodium hydrogen maleate. An excess of base has been discovered to increase the speed of the reaction but also it increases the speed of the reversion of the desired ODS product to fumarate. In general, the reactant ratios in the reaction mixture in accordance with this invention in terms of malic acid/ maleic acid/calcium hydroxide/sodium hydroxide mole ratio is typically in the range of 1/2.2/1.6/3.4. These ratios are the usual mid-point of ranges commonly employed and found to provide optimum results in accordance with this invention and can vary widely.

The reaction temperature of the process of this invention appears to control the rate of reaction and thus the amount of time required to produce optimum results. Typically, at 80° C. the reaction proceeds to completion in from about 1 to 3 hours for maximum malate conversion utilizing the abovementioned reactant ratios. When the reaction is run at about 70° C. maximum malate conversion occurs in from 2 to 6 hours and such conversion is slightly higher than is found at a reaction temperature of 80° C. Acceptable results have been obtained at higher temperatures (90°/100° C.) with reaction times of 1 hour or less; however, the amount of fumarate formed increases rapidly.

The aqueous reaction mixtures forming ether carboxylates by the reaction of maleate and malate according to prior art methods contain from about 31% to about 41% by weight, more preferably 36% to about 40% by weight maleate and malate. The reaction mixture in accordance with this invention may contain from about 40% to 75%, by weight of the maleate and maleate salts. The progress of the reaction is typically determined by applying techniques such as High Performance Liquid Chromatography (HPLC) whereby the yield of ODS and the levels of maleate and malate reactants and of fumarate by-products and other individual reaction product can be monitored. The reaction is terminated by cooling typically to below 50° C. and preferably to ambient temperature. In prior art reactions, yields of at least 50% of the ODS based upon malate were obtained. However, in accordance with the process of the present invention the yields can be higher and product processing shorter due to adjustment of reactant ratios and to the convenient recovery of unreacted starting materials. Because starting materials are conveniently recovered, greater freedom of reactant ratios in the initial reaction mixture are obtained to the benefit of greater conversion and shorter processing time to provide a final product. It is reported that the complex sodium/calcium salts of the maleate and malate reactants as well as the ODS product formed in situ provide much higher solubilities of the reaction product than when single-metal calcium salts are employed. Such solubility is advantageous because it allows convenient high-concentration processes, easier pumping and handling properties.

In accordance with this invention sodium hydrogen maleate is easily recovered from the reaction product by reducing the pH of the reaction product with maleic acid to a range of from about 4 to about 6 whereby the unreacted maleic acid salt precipitates as sodium hydrogen maleate and is easily recovered for recycle to the synthesis reaction. Such process will be more fully described below.

The recovery of maleate and malic salt is achieved by lowering the pH of the reaction mixture whereby sodium hydrogen maleate precipitates. In the preferred embodiment the reaction mixture is also cooled and diluted with water. Maleic acid is added so as to bring the combined synthesis mass and acid to a final pH in the range of from about 4.5 to 5.5, preferably slightly below 5.2.

In the process of this invention, the acid substance may be added to the crude reaction mass. Alternately, the reaction mass may be added to a heel containing the acid substance. In a further process of this invention, the acid substance and the reaction mass may be added concurrently into a mixing vessel. Sufficient water is added to the reaction mass and/or acid material so that the final concentration of desired ether carboxylate in the completed mixture is from about 40% to about 55%, by weight.

Sufficient acid is added t reach the preferred pH range of from about 4.5 to about 5.5 and the precipitated reaction mass is cooled to below 50° C. Preferably the reaction mass is cooled to a range of from just above the freezing point of the mixture to about 40° C., most practically to about 20° C. to about 30° C. Satisfactory filtration rates are thus obtained in large scale production. In a preferred mode, cooling the reaction product from the 80° C. reaction temperature to 65° C. over 30 minutes is followed by slow cooling to from about 30° C. to about 40° C. The suspension is then allowed to rest for about 30 minutes. The slurry is preferably cooled slowly with mild or slow agitation so as to grow particles which can be filtered in an appropriately short time. Other methods of acid addition such as are noted above can also be employed with appropriate adjustment of precipitation conditions.

Removal of the precipitated acid salt may take any form practical and typically is performed by continuously drawing the slurry from the precipitator to a belt or drum filter or centrifuge. Other forms of removal such as decantation, etc. may also be employed. The filtrate contains the ether carboxylate in salt form. In a preferred embodiment the filtrate is transferred to another precipitator for removal of the calcium cations in the form of calcium carbonate.

Throughout pH reduction, cooling is required to maintain the temperature of the reaction mixture in the desired range of about 35° C. As noted above, the reaction mixture is held for about 30 to about 40 minutes after final pH reduction to allow crystal formation. The larger agglomerates are more easily separated from the reaction mixture.

CALCIUM CARBONATE PRECIPITATION

After removal of the insoluble acid salt or salts as described above, the filtrate from such operation is recovered and purified for use as detergent builder. In a preferred embodiment, calcium is removed either batchwise or preferably continuously. Typically, the filtrate from the above-mentioned step is pH adjusted with a base, preferably sodium hydroxide, as it is being fed into a calcium carbonate precipitator to bring the pH of the solution into a range of from about 10 to about 12, preferably from about 10 to about 10.5. The pH adjustment may be performed either in the precipitator or in a separate vessel if desired. The pH adjusted material is maintained in the range of from about 75° C. to about 110° C., preferably at about 90° C. to 100° C. Concurrently a solution of a basic carbonate, preferably sodium carbonate, preferably at a concentration of about 25%, is added to the precipitator to provide an overall mole ratio of carbonate to calcium of 1.3:1.

Alternatively, calcium carbonate is removed by increasing the mole ratio of carbonate ion to calcium ion without change in pH.

Although this invention is described with respect to carbonate precipitation using the preferred sodium cation, it is to be understood that other suitable cations may also be employed to obtain precipitation of calcium carbonate. Other cations useful in the process of this invention include potassium, ammonium or organo substituted ammonium. Other salts may be employed to obtain the calcium carbonate precipitate and includes sodium bicarbonate and mixtures of carbonates and bicarbonates.

During the precipitation of calcium carbonate it is preferred that water is continuously removed from the slurry to maintain the concentration of the organic acid salts in the range of from about 30% to about 50% by weight. Filtration of the precipitated calcium carbonate may take any form practical and typically is performed by continuously drawing the slurry from the precipitator to a centrifuge or to a belt or drum filter. The filtrate contains the desired ether carboxylate mostly as the alkaline salt along with minor amounts of raw material and by-products.

The wet cake from the separation is mechanically reslurried with water to form an approximately 50% calcium carbonate slurry for recycle to the synthesis reaction. The recovered carbonate may be added directly to the ether carboxylate synthesis reactor or together with recovered, unreacted tartrate and maleate. Preferably, the recovered calcium carbonate is converted to calcium maleate in a separate vessel before return to the synthesis reaction.

To further illustrate the process of the present invention there is described below nonlimiting preferred embodiments. Unless otherwise noted all percentages are by weight.

EXAMPLE 1

Into a 1 liter Ace reactor equipped with a thermometer, mechanical stirrer, condenser and a sample port there is placed 156.5g of water. Then 240g of 50% sodium hydroxide solution (3.0 moles) were added. D,L-malic acid (134.0g, 1.0 mole) Was added slowly to this mixture. At the end of the addition, the temperature had risen to ca. 85-90° C. Calcium hydroxide (118.4g, 1.6 mole) was added as a solid to the solution and the slurry stirred vigorously. Maleic anhydride (196.0g, 2.0 moles) was added as a solid at such a rate that the temperature was maintained between 80° and 95° C. (ca. 15 min.) On completion of this addition, the reaction mass comprised about 60% solids, 40% water. The partially cleared (translucent) mass was stirred and held at 80°-85° C. for three hours. At the end of the reaction period a solution of maleic acid, prepared by dissolving 98g (1.0 mole) of maleic anhydride in 200g water at 65°-70° C. was added to the hot reaction mixture. The pH after the addition of maleic acid was measured at 4.94. The reaction mass was cooled to about 30° C. and filtered. The crystals of sodium hydrogen maleate were washed with about 150 ml water and air dried. The filter cake weighed 432.3g and the filtrate weighed 560.6g. Both were sampled for analysis.

A solution of 220.5g (2.08 moles) of sodium carbonate in 600 ml water was prepared and heated to about 80° C. The filtrate from above was slowly added to the sodium carbonate solution at 80° C. to precipitate calcium carbonate from the reaction mixture. The resulting slurry was heated at 80°-85° C. for one hour and then filtered hot. The calcium carbonate filter cake was washed with about 50 ml water. The filtrate, containing the desired ODS as the tetrasodium salt was analysed. Analysis by x-ray fluorescence indicates only 0.056% calcium present in the filtrate. Analytical results of the reaction mixture (normalized weight %) appear in Table XVII below.

TABLE XVII

| SAMPLE: COMPONENT | END OF REACTION | AFTER MALEATE REMOVAL | AFTER CARBONATE REMOVAL |
|---|---|---|---|
| Disodium Malate | 6.22 | 8.34 | 8.41 |
| Disodium Maleate | 28.75 | 2.18 | 2.37 |
| Disodium Fumarate | 5.07 | 7.15 | 7.11 |
| Tetrasodium Oxydisuccinate | 59.96 | 82.33 | 82.11 |
| Malate Conversion (Mole %) | 83.54 | 83.87 | 83.72 |

This example shows that maleic acid can be used to remove sodium hydrogen maleate from the reaction and still maintain acceptably low residual levels of maleate in the final product.

EXAMPLE 2

Tests were conducted to determine the characteristics of maleate hydration with and Without the presence of sodium hydrogen maleate. Hydration reactions were conducted at 120° C. for times noted in the table. In Part A maleic anhydride alone was added to water. In Part B maleic anhydride and sodium hydrogen maleate as recovered in the procedure of Example 1 were combined and in Part C maleic anhydride, sodium hydrogen maleate and fumaric acid were combined. In the table below the amount of feed material is expressed in grams. The results shown in Table I below indicates that a higher ratio of sulfuric acid is required to provide equivalent conversion to malate when sodium hydrogen maleate is present, Part C.

TABLE I

Part A

| Maleic Acid | Feed $H_2O$ | Cat | Catalyst Type | Maleic/Cat. Mole Ratio | Rxn. Time (hrs.) | Mole % Maleic Conv. to Malate | Mole % Maleic Conv. to Fumarate | Mole % Unconv. Maleate |
|---|---|---|---|---|---|---|---|---|
| 1.240 | 1.240 | — | none | — | 20 | 19.6 | 29.1 | 51.3 |
| 1.130 | 1.130 | 0.260 | $H_2SO_4$ | 3.67 | 20 | 65.1 | 24.3 | 10.6 |
| 1.095 | 1.579 | 0.146 | $Ca(NO_3)_2$ | 10.61 | 20 | 29.6 | 64.8 | 5.6 |
| 1.160 | 1.160 | — | none | — | 94 | 49.4 | 41.1 | 9.4 |
| 1.225 | 1.225 | 0.290 | $H_2SO_4$ | 3.57 | 94 | 81.0 | 18.6 | 0.4 |
| 1.195 | 1.648 | 0.137 | $Ca(NO_3)_2$ | 12.36 | 94 | 62.0 | 36.2 | 1.8 |

Part B

| Maleic | Feed NaH | Catalyst | Total Maleic/Cat. | Rxn. Time | Mole % Maleic Conv. To | To |

TABLE I-continued

| Acid | Maleate | H₂O | Cat. | type | Mole Ratio | (hrs.) | Malate | Fumarate |
|---|---|---|---|---|---|---|---|---|
| 0.344 | 0.410 | 1.396 | — | none | — | 20 | 14.7 | 47.1 |
| 0.351 | 0.417 | 1.422 | 0.280 | H₂SO₄ | 2.11 | 20 | 26.4 | 50.2 |
| 0.360 | 0.429 | 1.931 | 0.137 | Ca(NO₃)₂ | 7.44 | 20 | 21.8 | 52.5 |
| 0.372 | 0.442 | 1.506 | — | none | — | 94 | 54.9 | 40.2 |
| 0.380 | 0.452 | 1.538 | 0.250 | H₂SO₄ | 2.57 | 94 | 47.1 | 51.9 |
| 0.369 | 0.438 | 1.953 | 0.140 | Ca(NO₃)₂ | 7.44 | 94 | 62.8 | 32.5 |

Part C

| Maleic Acid | Feed NaH Maleate | Fumaric Acid | H₂O | Cat | Catalyst type | Total Maleic/Cat. Mole Ratio | Rxn. Time (hrs.) | Mole % Conv. of Maleic & Fumaric to | |
|---|---|---|---|---|---|---|---|---|---|
| | | | | | | | | Malate | Fumarate |
| 0.148 | 0.440 | 0.074 | 1.788 | — | none | — | 16 | 3.2 | 26.7 |
| 0.146 | 0.435 | 0.073 | 1.766 | 0.630 | H₂SO₄ | 0.78 | 16 | 22.2 | 17.6 |
| 0.145 | 0.431 | 0.073 | 1.751 | — | none | — | 90 | 16.2 | 57.5 |
| 0.144 | 0.430 | 0.072 | 1.744 | 0.600 | H₂SO₄ | 0.81 | 90 | 71.5 | 21.0 |

EXAMPLE 3

The conversion of sodium hydrogen maleate to malic acid was provided under different catalyst conditions. From the results, presented in Table II below it is shown that hydrochloric acid provides greater conversion to malate than sulfuric acid but that sulfuric acid, at higher ratio to maleate improves conversion to malate. As in Example 1, the hydration reaction was conducted at 120° C. The feed material is listed in weight percent of the reaction mixture. In the first test, Part A, no catalyst was employed. In the second test, Part B, sulfuric acid was employed at a higher ratio than reported above and in the third test, Part C hydrochloric acid was employed as the catalyst in place of sulfuric acid.

TABLE II

| Reaction Time | Normalized Wt. % as (Na salt) | | | Mole % Maleic Conv. | | Feed Material | (Wt. %) |
|---|---|---|---|---|---|---|---|
| | Malate | Maleate | Fumarate | To Malate | To Fumarate | | |
| Part A | | | | | | | |
| 0 | 0.00 | 100.00 | 0.00 | 0.00 | 0.00 | NaH Maleate | 22.74% |
| 4 | 0.00 | 99.71 | 0.29 | 0.00 | 0.29 | Water | 77.26 |
| 10½ | 0.00 | 99.58 | 0.42 | 0.00 | 0.42 | | |
| 22 | 0.00 | 99.27 | 0.73 | 0.00 | 0.73 | | |
| 47 | 0.00 | 98.01 | 1.99 | 0.00 | 1.99 | | |
| Part B | | | | | | | |
| 0 | 0.00 | 100.00 | 0.00 | 0.00 | 0.00 | NaH Maleate | 22.74% |
| 4 | 2.99 | 90.52 | 6.49 | 2.70 | 6.51 | Water | 77.26 |
| 10½ | 8.76 | 72.78 | 18.46 | 7.94 | 18.62 | H₂SO₄ catalyst | |
| 22 | 15.37 | 59.71 | 24.92 | 14.03 | 25.31 | Mole Ratio | |
| 47 | 24.38 | 29.14 | 46.48 | 24.47 | 47.65 | Diacid/H₂SO₄ = 1.33 | |
| Part C | | | | | | | |
| 0 | 0.00 | 100.00 | 0.00 | 0.00 | 0.00 | NaH Maleate | 22.74% |
| 4 | 9.07 | 30.44 | 60.49 | 8.23 | 61.05 | Water | 77.26 |
| 10½ | 17.11 | 14.26 | 68.73 | 15.65 | 69.94 | HCl catalyst | |
| 22 | 25.84 | 1.30 | 72.86 | 23.85 | 74.81 | Mole Ratio | |
| 47 | 42.13 | 1.03 | 56.85 | 39.55 | 59.38 | Diacid/HCl = 0.71 | |

There has been described a novel process of general application to the production ODS. While the process has been described with reference to specific compounds, no intention is made by such reference to limit the scope of this invention unless expressly stated. Various modifications may be made in the materials and sequence of process steps as well as process combinations which are adapted to suit the various reactants and products without departing from this invention.

I claim:

1. A process for preparing the alkali metal salt of oxydisuccinic acid which comprises reacting in an alkaline reaction medium the salts of maleic acid and malic acid in the presence of a calcium ion catalyst, reducing the pH of the reaction product to a range of from about 4 to about 6 whereby unreacted starting acid salts precipitate, including sodium hydrogen maleate, recovering said maleate and hydrating it to malic acid salt for reuse in said process, wherein the hydration takes place in the presence of a catalyst for hydration.

2. The process of claim 1 wherein the catalyst is selected from the group consisting of sulfuric acid, hydrochloric acid and calcium nitrate.

3. The process of claim 1 wherein the hydration takes place in the presence of maleic acid.

4. The process of claim 2 wherein the oxydisuccinic acid salt is 2,2'-oxydisuccinate.

5. The process of claim 2 wherein the hydration reaction is carried out at a temperature in the range of from about 100° C. to about 175° C.

6. The process of claim 5 wherein the catalyst is sulfuric acid.

7. The process of claim 5 wherein the catalyst is hydrochloric acid.

8. The process of claim 6 wherein the mole ratio of diacid equivalent to hydration catalyst is above 1.

9. The process of claim 7 wherein the mole ratio of diacid equivalent to hydration catalyst is about 7:1.

10. The process of claim 2 wherein the catalyst is calcium nitrate.

11. The process of claim 10 wherein the mole ratio of diacid equivalent to hydration catalyst is above 7.

12. The process of claim 1 wherein the oxydisuccinic acid salt is a 2,2'-oxydisuccinate.

13. The process of claim 1 wherein the mole ratio of maleic salt to malate salt is in excess of 1.

14. The process of claim 3 wherein the maleic acid is added to the reaction mixture as maleic anhydride and sufficient water is present to hydrolyze the anhydride.

* * * * *